United States Patent
Darcey (10) Patent No.: US 9,504,597 B2
(45) Date of Patent: Nov. 29, 2016

(54) FUNCTIONAL CAST THERAPY PRODUCT AND METHOD

(71) Applicant: BSN medical, Inc., Charlotte, NC (US)

(72) Inventor: Thomas D. Darcey, Mooresville, NC (US)

(73) Assignee: BSN MEDICAL, INC., Charlotte, NC (US)

( * ) Notice: Subject to any disclaimer, the term of this patent is extended or adjusted under 35 U.S.C. 154(b) by 337 days.

(21) Appl. No.: 14/196,226

(22) Filed: Mar. 4, 2014

(65) Prior Publication Data
US 2015/0250636 A1 Sep. 10, 2015

(51) Int. Cl.
*A61F 5/00* (2006.01)
*A61F 5/058* (2006.01)

(52) U.S. Cl.
CPC ............... *A61F 5/058* (2013.01); *A61B 50/30* (2016.02)

(58) Field of Classification Search
CPC ....... A61F 13/04; H03H 9/0528; E04B 5/04; E04C 2/384; B65D 7/00
USPC ......................................................... 602/5–8
See application file for complete search history.

(56) References Cited

U.S. PATENT DOCUMENTS

| 3,800,789 | A | * | 4/1974 | Schloss | A61F 5/0585 128/DIG. 15 |
| 3,826,252 | A | * | 7/1974 | Laico | A61F 13/04 602/11 |
| 3,867,931 | A | * | 2/1975 | Babka | A61F 15/02 602/9 |
| 4,793,330 | A | * | 12/1988 | Honeycutt | A61L 15/07 523/105 |
| 5,016,622 | A | | 5/1991 | Norvell | |
| 2012/0145303 | A1 | * | 6/2012 | McClarnan | B44C 1/10 156/60 |

OTHER PUBLICATIONS

International Search Report dated Aug. 1, 2014 for International Application No. PCT/US2014/027291.

* cited by examiner

*Primary Examiner* — Michael Brown
(74) *Attorney, Agent, or Firm* — Shumaker, Loop & Kendrick, LLP (57) ABSTRACT

A kit for containing components for fabricating functional casts, and including a box, and a length of liner for being placed next to the skin of the body part to be immobilized; a moisture-proof package containing a length of cast tape of the type impregnated with a moisture-curable resin that remains in a flexible, comfortable state until activated and hardened into a rigid state by exposure to moisture; at least one strap for securing the cast onto the body part being immobilized and a length of adhesive edger material for enclosing raw edges of the hardened cast tape for protecting the skin of the cast wearer from exposure to the cast tape, each of which is contained in the box.

13 Claims, 8 Drawing Sheets

FUNCTIONAL CAST THERAPY PRODUCT AND METHOD

TECHNICAL FIELD AND BACKGROUND OF THE INVENTION

The present invention relates to a functional cast therapy product, and a method of using the product to create a therapeutic cast on a patient. The product that is the subject of the invention is in "kit" form, and substantially improves the efficiency of creating a cast or splint from the various components medically required to achieve the desired therapeutic result.

Functional casts are casts formed of conformable cast tape and techniques that permit rigidity where immobilization is required, but which also permit a degree of flexibility in other areas of the body part where immobilization is not necessary. This type of cast stabilizes joints and limbs without negatively affecting adjoining soft tissues or joints. Muscle function is maintained during healing, leading to a decreased need for physiotherapy.

The conformable cast tape used with this technique is typically polyethylene ("PE") cast tape that, unlike fiberglass, has a degree of flex after hardening into its therapeutic, "in use" condition. PE cast tape is coated or impregnated with a curable resin and stored in low moisture conditions in a moisture-proof pouch. Upon exposure to water, the PE cast tape is hardened over a period of time that permits application to and conformity with the joint or limb to be immobilized.

Use of PE cast tape permits the cast to be used as a single therapeutic product. Initially, the cast as applied can be constructed as a primary cast. Later during recovery, the cast can be removed with scissors, and adjusted to accommodate for reduction of edema or for muscle atrophy. Alternatively, the cast can be created initially for use with chronic conditions such as arthritis, sprains and the like.

In either usage, these casts are light-weight and easy to clean.

In contrast to conventional casts, functional casts require a number of distinct components, some of which are typically sold in long, multi-use rolls. These materials must be available for use at a specific location, are subject to wastage and make the actual cost of a single cast hard to capture for accounting or billing purposes. Typically, a technician will be required to go from place-to-place within the facility to gather together the necessary materials. For this reason, in many situations, as when a cast technician must travel outside a medical facility to apply or adjust a cast, other types of casts are used.

SUMMARY OF THE INVENTION

It is therefore an object of the present invention to provide a functional cast kit that contains the components necessary to apply a functional cast to a patient.

It is a further object of the invention to provide a functional cast kit that contains the components necessary to apply a functional cast to a patient, where the components are pre-fabricated and sized to permit application of a single cast without waste.

It is a further object of the invention to provide a method of applying a functional cast that includes the step of preparing a kit that contains the components necessary to apply a functional cast to a patient.

It is a further object of the invention to provide a method of applying a functional cast that includes the step of preparing a kit that contains the components necessary to apply a functional cast to a patient, where the components are pre-fabricated and sized to permit application of a single cast without waste, and using the pre-fabricated and sized components to apply a single functional cast to a patient.

These and other objects and advantages of the invention are achieved by providing a kit for containing components for fabricating functional casts, and including a box, and a length of liner for being placed next to the skin of the body part to be immobilized; a moisture-proof package containing a length of cast tape of the type impregnated with a moisture-curable resin that remains in a flexible, comformable state until activated and hardened into a rigid state by exposure to moisture; at least one strap for securing the cast onto the body part being immobilized and a length of adhesive edger material for enclosing raw edges of the hardened cast tape for protecting the skin of the cast wearer from exposure to the cast tape, each of which is contained in the box.

According to one embodiment of the invention, at least one pad is provided for being placed between the cast tape and the body part to provide additional protection to bony prominences.

According to another embodiment of the invention, the at least one strap includes a length of loop touch fastener material and a length of complementary touch fastener hook material.

According to another embodiment of the invention, the length of loop touch fastener is stretchable, and the length of hook material has an adhesive on one side for being attached to the cast tape.

According to another embodiment of the invention, the liner is a material selected from the group consisting of a terry cloth stockinette and a water resistant cast padding.

According to another embodiment of the invention, the edger material includes a moisture resistant fleece material with an adhesive on one side for being adhered to the cast tape.

According to another embodiment of the invention, a length of protective cutting strip is provided in the kit for being applied to the body part under the liner.

According to another embodiment of the invention, a kit containing components for fabricating a functional cast is provided and includes a length of liner selected from the group consisting of a terry cloth stockinette and a water resistant cast padding for being placed next to the skin of the body part to be immobilized, a moisture-proof package containing a length of cast tape of the type impregnated with a moisture-curable resin that remains in a flexible, comformable state until activated and hardened into a rigid state by exposure to moisture, a length of stretchable loop touch fastener material and a length of complementary touch fastener adhesive hook material, at least one pad for being placed between the cast tape and the body part to provide additional protection to bony prominences, a length of adhesive fleece edger material for enclosing raw edges of the hardened cast tape for protecting the skin of the cast wearer from exposure to the cast tape, and suitably-sized package such as a box for containing the materials in kit form until use.

According to another embodiment of the invention, the method includes the steps of providing a kit containing components for fabricating functional casts, including a length of liner for being placed next to the skin of the body part to be immobilized, a length of cutting strip, a moisture-proof package containing a length of cast tape of the type impregnated with a moisture-curable resin that remains in a flexible, comformable state until activated and hardened into a rigid state by exposure to moisture, at least one strap for securing the cast onto the body part being immobilized, and a length of adhesive edger material for enclosing raw edges of the hardened cast tape for protecting the skin of the cast wearer from exposure to the cast tape. The liner is removed from the kit and the liner is applied to a body part to be immobilized. The length of cutting strip is inserted between the liner and the body part. The moisture-curable cast tape is removed from the package, the moisture-curable resin activated with water and applied to the body part to form a cast when hardened. When hardened, the cast tape is cut along a line defined by the length of the cutting strip, spread and removed from the body part. The cast is further cut as needed to customize the fit to the body part. Edger material is applied to raw edges of the cast tape. The cast is reapplied and secured to the body part.

According to another embodiment of the invention, the step of securing the cast to the body part includes the steps of providing in the kit a length of stretchable loop touch fastener material and a length of complementary touch fastener adhesive hook material, adhering the hook touch fastener to the cast, wrapping the loop touch fastener around the cast and adhering the loops to the hooks.

According to another embodiment of the invention, the method includes the steps of providing padding material in the kit, removing the padding from the kit and inserting the padding under the cast tape in an area defined by a bony prominence.

According to another embodiment of the invention, the fabricated cast is selected from the group consisting of a forearm functional cast, short thumb spica cast, teardrop hand splint, boxer hand splint, humeral cast, long arm cast, great toe cast, metatarsal shoe, cast shoe with ankle extension, ankle stirrup, short leg, and short version knee immobilizer/Tutor cast.

BRIEF DESCRIPTION OF THE DRAWING FIGURES

The present invention is best understood when the following detailed description of the invention is read with reference to the accompanying drawings, in which.

DETAILED DESCRIPTION OF THE PREFERRED EMBODIMENT

Figure 1:
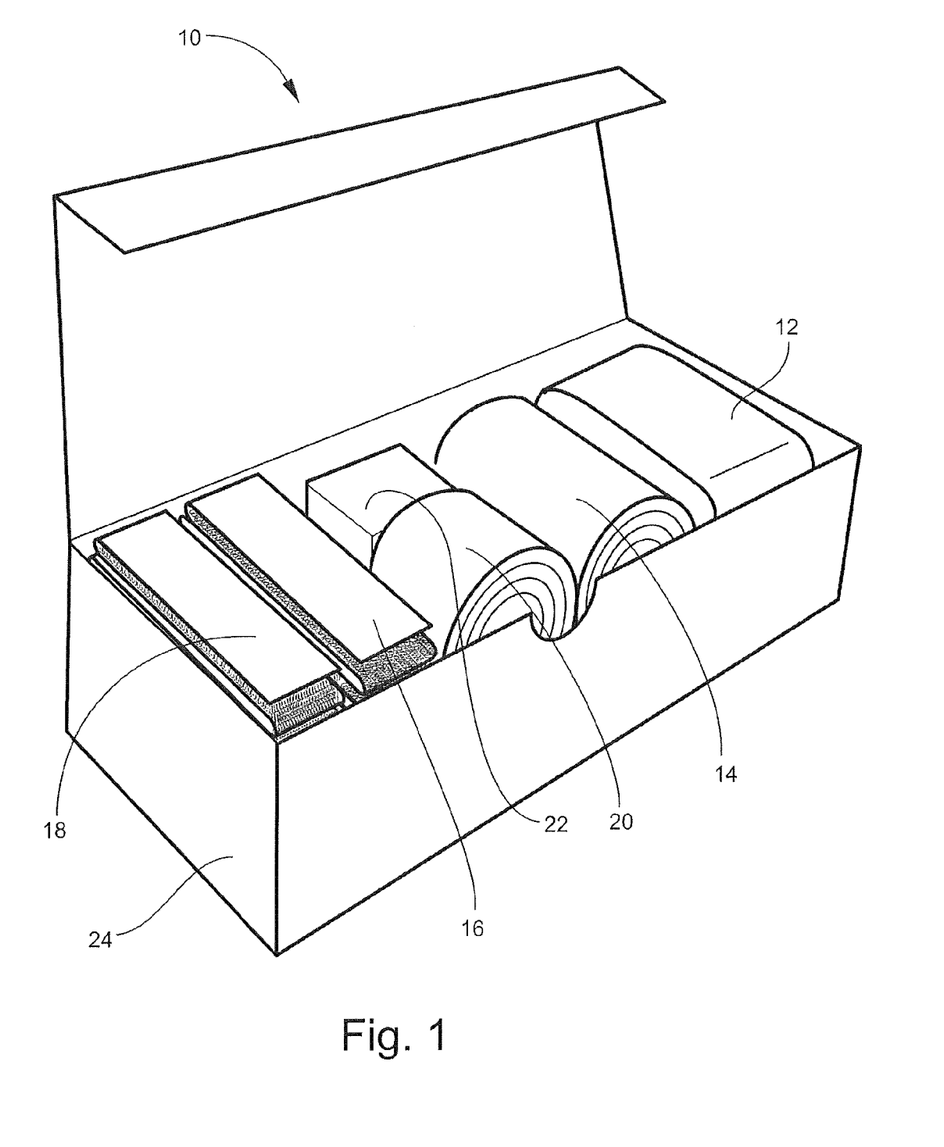
FIG. 1 is a perspective view of a kit containing the components needed for a single functional cast according to one preferred embodiment of the invention.

Referring now to FIG. 1, a functional cast kit 10 according to one embodiment of the invention is illustrated at reference numeral 10. While the contents of the kit 10 can vary based on the specific size and type of cast to be fabricated, for purposes of illustration the kit 10 includes a packaged roll of PE cast tape 12, a roll of terry liner 14, a strip of stretch loop touch fastener 16, a strip of adhesive hook touch fastener 18, a roll of fleece edger 20, and an adhesive terry foam pad, felt pad, or cohesive bandage 22 to use if needed to cover and further protect bony prominences to reduce pressure points. These contents are packaged in a suitably-sized box 24. Other alternatives include one or more straps with buckles to secure the cast, or a single touch fastener strap with both hooks and loops positioned to allow the strap to overlap and be secured in place. A preferred PE cast tape is Delta-Cast® Conformable manufactured by BSN medical, Inc. Preferred liners are Delta-Dry® water resistant cast padding or Terry-Net™ stockinette manufactured by BSN medical, Inc. Preferred hook and loop straps are Terry-Net™ adhesive hook and stretch loop products manufactured by BSN medical, Inc. A preferred fleece edger is Terry-Net™ adhesive fleece edger manufactured by BSN medical, Inc. A preferred adhesive cloth and foam liner is Terry-Net™ adhesive cloth and foam liner manufactured by BSN medical, Inc. A preferred adhesive felt padding is Terry-Net™ adhesive felt padding manufactured by BSN medical, Inc. A preferred cohesive bandage is Co-Plus® LF cohesive bandage manufactured by BSN medical, Inc.

As described below, the end result of cast and splint fabrication using the kit 10 and the method steps described in this application is essentially the same as if components in their conventional form are used, but with greater ease, efficiency and economy.

In addition to the materials in the kit 10, a technician will typically use gloves, cast shears, a felt tip marker and a protective cutting strip, all of which are reusable and therefore not necessary to be contained in the kit 10. However, if single use gloves are desired, they can be included.

Figure 2:
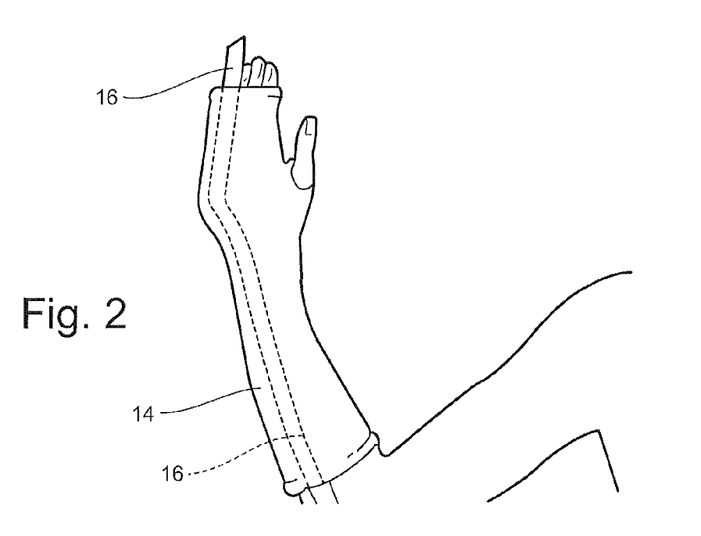
FIGS. 2-9 are sequential views of method steps used to fabricate a forearm functional cast.
Figures 3, 4:
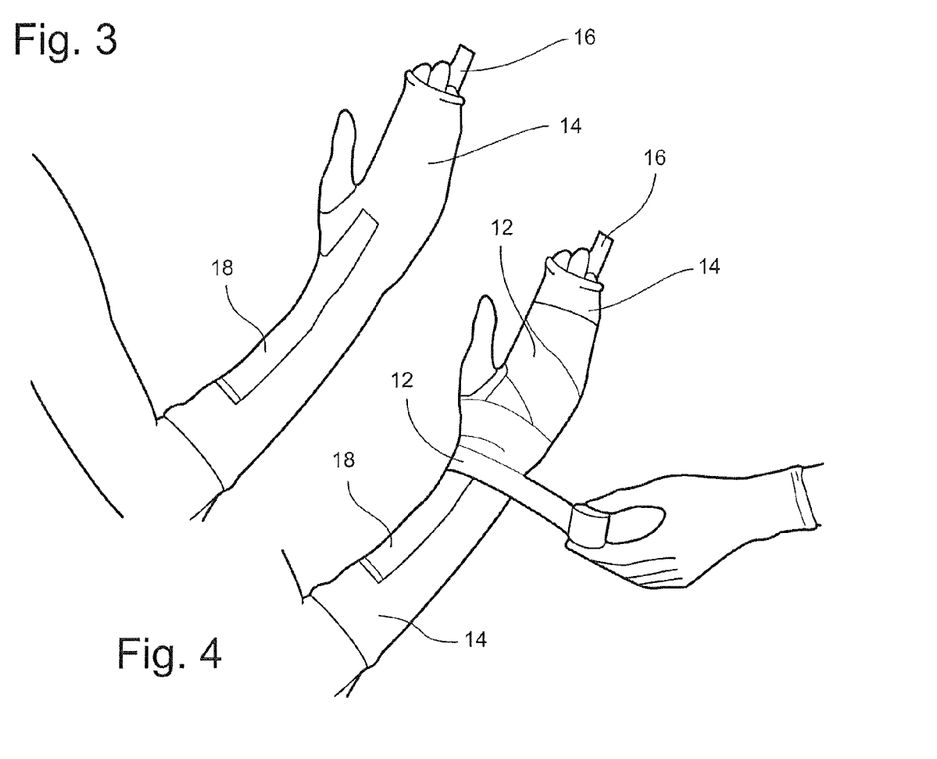
Figure 5:
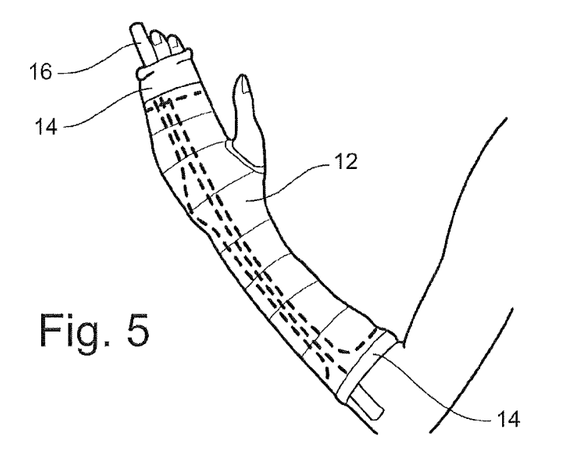
Figures 6, 7:
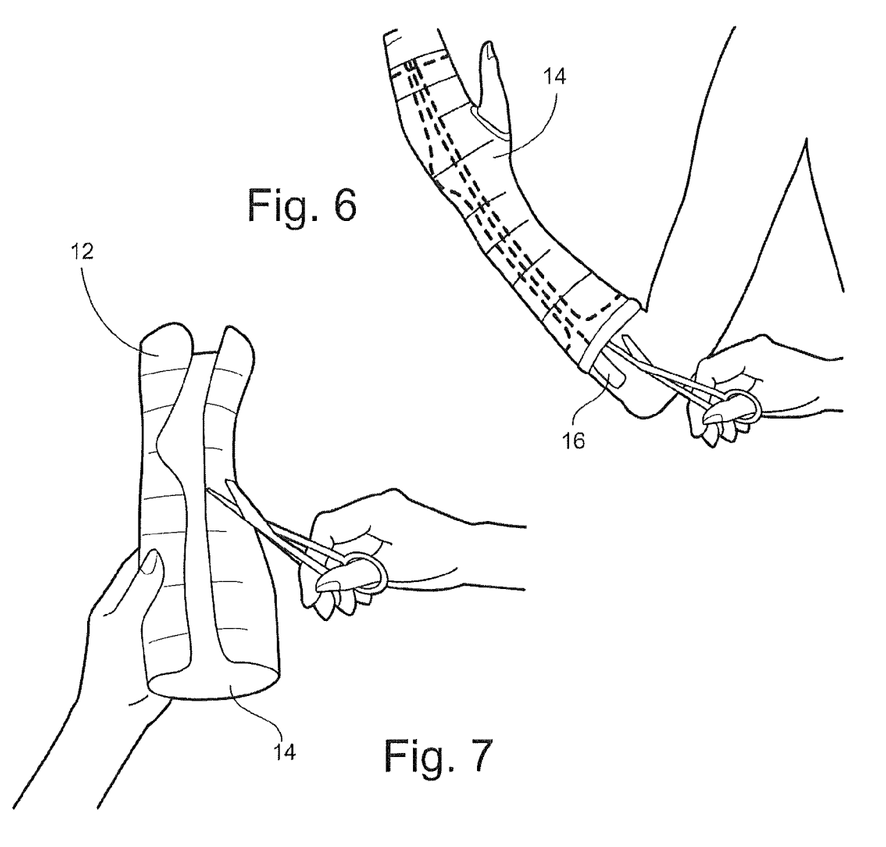

Referring now to FIGS. 2-9, the method of applying the contents of the kit 10 for forming a short arm cast 26 (FIG. 9) is illustrated. The terry liner 14 is removed from the box 24 and as shown in FIG. 2, applied with the padded side next to the patient's skin. If needed, additional padding can be applied to the ulnar styloid. A protective cutting strip 16 is inserted on the dorsal side of the arm under the liner 14. The cast tape 12 is removed from the box 24, removed from the moisture-proof package and activated by wetting while wearing gloves. As shown in FIG. 3, 2-3 layers of reinforcing strips 18 may be cut from the cast tape 12 and applied as shown. The cast tape 12 is then wrapped onto the arm beginning at the fingers and continuing proximally up the arm, overlapping by about 50 percent and ending two inches from the antecubital space, as shown in FIG. 4. The cast tape 12 is smoothed onto the arm and the arm is conformed into the correct position. As shown in FIG. 5, after the cast tape 12 has set, a marker such as a felt-tip pen is used to draw the desired cutting lines (shown as dashed lines) to customize the fit of the cast. The cast is removed by placing cast shears between the terry liner 14 and the cutting strip 16 and cutting along the entire length of the cast, as shown in FIG. 6. The cast can then be removed by spreading the cast along the cut lines and making further comfort cuts on the palmer and dorsal sides proximal to the metacarpal heads, as shown in FIG. 7.

Figures 8, 9, 10:
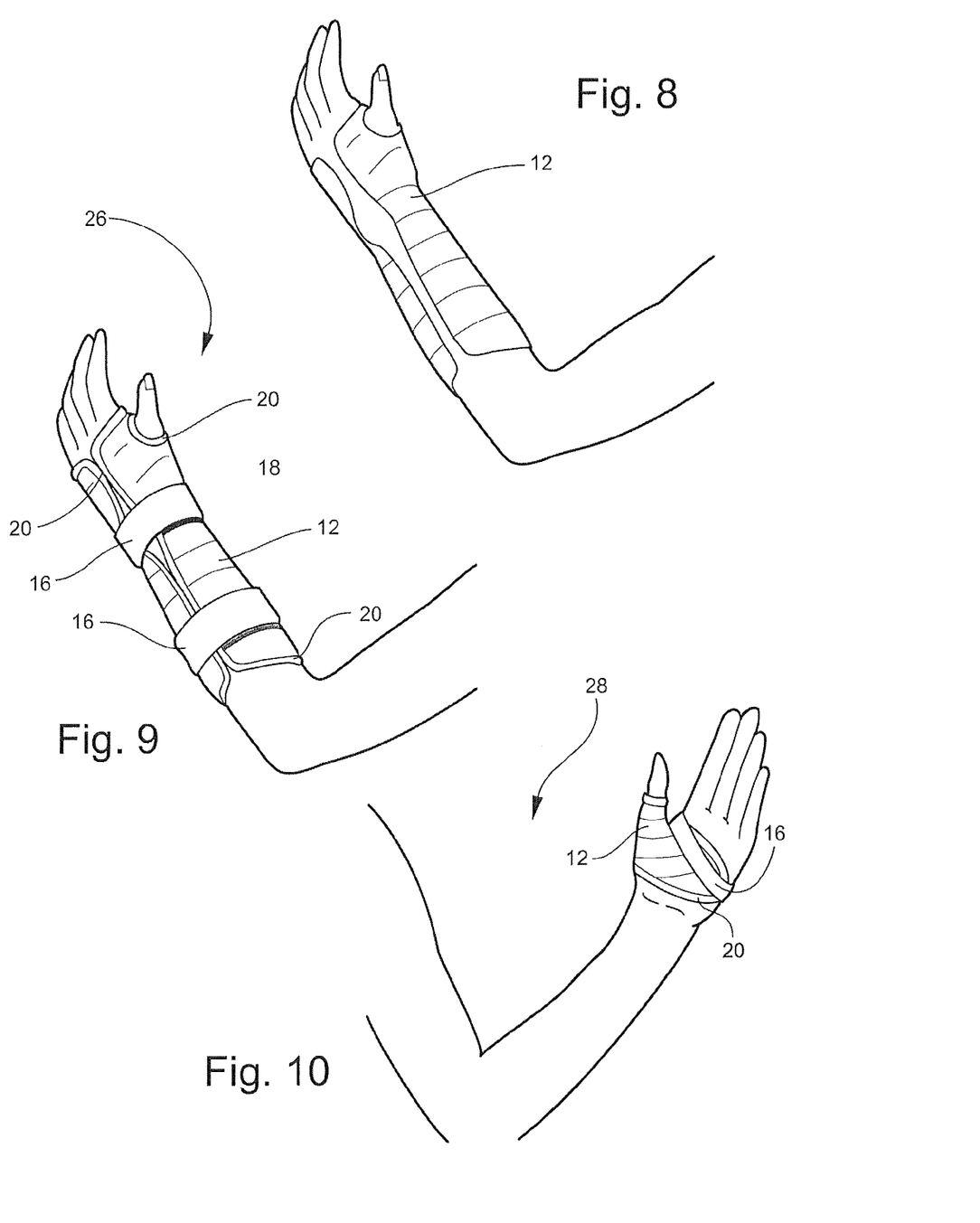
FIG. 10 is a view of a short thumb spica cast fabricated using components of the kit and the method steps according to one preferred embodiment of the invention.

Referring to FIG. 8, the cast is reapplied to the arm to test the fit, and any necessary further cuts are made. As is shown in FIG. 9, the fleece edger fabric 20 is removed from the box 24 and used to cover and protect the raw edges around the periphery of the cast, and the length of adhesive hook touch fastener is attached to the outer surface of the cast in at least two spaced-apart positions. Lengths of loop touch fastener 16 are then used to secure the cast 26 to the arm, as shown. Additional padding 22 can be added beneath the cast 26 to protect bony prominences to reduce pressure points.

The contents of the kit 10 can vary depending on the particular end use, the size of the patient and similar factors. The basic principle remains that casts and splints can be much more efficiently and effectively applied either in a medical facility or remotely if all of the necessary items are packaged together and already sized to the extent possible to prevent waste and unnecessary cutting during cast fabrication.

Further examples of casts and splints that can be fabricated using the kit 10 or similar kits are illustrated in FIGS. 10-20. Because the basic steps used in fabricating the cast or splint are similar, the individual sequential drawings of the type provided for the short arm cast 26 are omitted for brevity in the remaining examples.

FIG. 10 illustrates a short thumb spica cast 28 fabricated using components of the kit 10 and the method steps according to one preferred embodiment of the invention. The terry liner 14 is removed from the box 24 and applied with the padded side next to the patient's skin. If needed, additional padding can be applied. A protective cutting strip 16 is inserted on the dorsal side of the arm under the liner 14. The cast tape 12 is removed from the box 24, removed from the moisture-proof package and activated by wetting while wearing gloves. The cast tape 12 is then wrapped onto the hand beginning at the thumb and continuing proximally to one finger width to the palm, overlapping by about 50 percent. The cast tape 12 is smoothed onto the hand and the hand is conformed into the correct position. After the cast tape 12 has set, a marker such as a felt-tip pen is used to draw the desired cutting lines to customize the fit of the cast. The cast is removed by placing cast shears between the terry liner 14 and the cutting strip 16 and cutting along the entire length of the dorsal side of the cast. The cast can then be removed by spreading the cast along the cut line and making further comfort cuts on the palmer crease and edges.

The cast is reapplied to the hand to test the fit, and any necessary further cuts are made. A fleece edger fabric 20 is removed from the box 24 and used to cover and protect the raw edges around the periphery of the cast. For light compression, edema control or if patient compliance is a concern, the cast is secured with a cohesive bandage from the kit 10 is used. Otherwise, the length of adhesive hook touch fastener is attached to the outer surface of the cast and lengths of loop touch fastener 16 is then used to secure the cast to the arm, as shown. Additional padding 22 can be added beneath the cast 28 to protect bony prominences to reduce pressure points.

Figures 11, 12, 13:
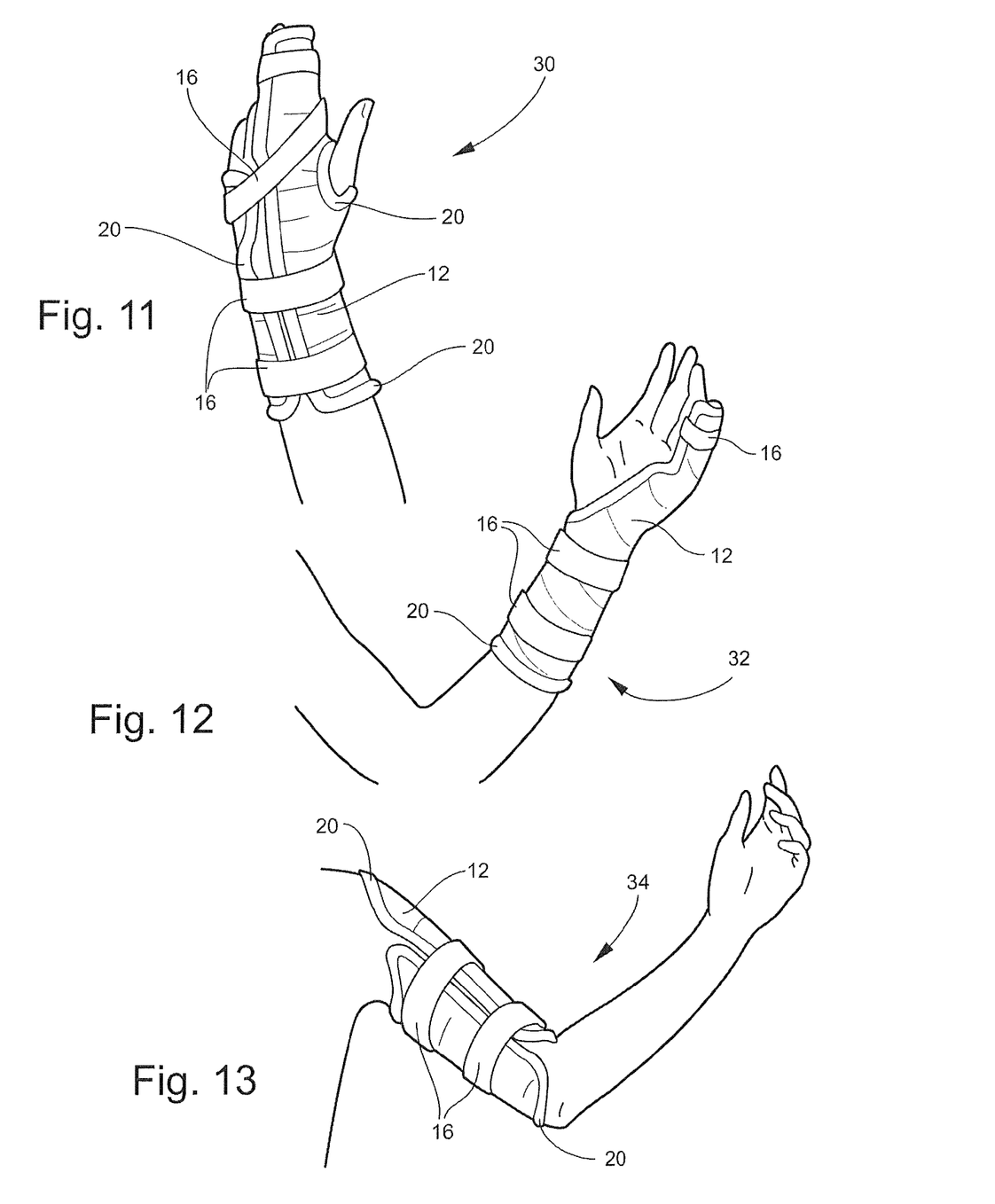
FIG. 11 is a view of a teardrop hand splint fabricated using components of the kit and the method steps according to one preferred embodiment of the invention.
FIG. 12 is a view of a boxer hand splint fabricated using components of the kit and the method steps according to one preferred embodiment of the invention.
FIG. 13 is a view of a humeral cast fabricated using components of the kit and the method steps according to one preferred embodiment of the invention.

FIG. 11 illustrates a teardrop hand splint 30 fabricated using components of the kit and the method steps according to one preferred embodiment of the invention. The terry liner 14 is removed from the box 24 and applied with the padded side next to the patient's skin. If needed, additional padding can be applied, including between the fingers. A protective cutting strip 16 is inserted under the liner 14. The cast tape 12 is removed from the box 24, removed from the moisture-proof package and activated by wetting while wearing gloves. Two or three layers of reinforcing strips 18 may be cut from the cast tape 12 and applied where the greatest rigidity is desired. The cast tape 12 is then wrapped onto the arm and hand beginning at the fingers and continuing proximally up the arm, overlapping by about 50 percent. The cast tape 12 is smoothed onto the hand and arm, and conformed into the correct position. After the cast tape 12 has set, a marker such as a felt-tip pen is used to draw the desired cutting lines to customize the fit of the cast. The cast 30 is removed by placing cast shears between the terry liner 14 and the cutting strip 16 and cutting along the entire length of the dorsal side of the cast. The cast can then be removed by spreading the cast along the cut line and making further comfort cuts on the palmer and dorsal sides proximal to the metacarpal heads.

The cast is reapplied to the hand to test the fit, and any necessary further cuts are made. A fleece edger fabric 20 is removed from the box 24 and used to cover and protect the raw edges around the periphery of the cast. For light compression, edema control or if patient compliance is a concern, the cast is secured with a cohesive bandage from the kit 10 is used. Otherwise, the length of adhesive hook touch fastener 18 is attached to the outer surface of the cast and lengths of loop touch fastener 16 is then used to secure the cast to the arm, as shown. Additional padding 22 can be added beneath the cast to protect bony prominences to reduce pressure points.

FIG. 12 illustrates a boxer hand splint 32 fabricated using components of the kit and the method steps according to one preferred embodiment of the invention. The terry liner 14 is removed from the box 24 and applied with the padded side next to the patient's skin. If needed, additional padding can be applied, including additional padding on the ulnar styloid. A protective cutting strip 16 is inserted under the liner 14. The cast tape 12 is removed from the box 24, removed from the moisture-proof package and activated while wearing gloves by wetting. Two or three layers of reinforcing strips 18 may be cut from the cast tape 12 and applied along the length of the little finger central joint to one hand width over the wrist on the ulnar side. The cast tape 12 is then wrapped onto the arm and hand beginning at the fingers and continuing proximally up the arm to the antecubital space, overlapping by about 50 percent. The cast tape 12 is smoothed onto the hand and arm, and conformed into the correct position. After the cast tape 12 has set, a marker such as a felt-tip pen is used to draw the desired cutting lines to customize the fit of the cast. The cast 32 is removed by placing cast shears between the terry liner 14 and the cutting strip 16 and cutting along the entire length of the dorsal side of the cast. The cast can then be removed by spreading the cast along the cut line and making further comfort cuts on the palmer and dorsal sides proximal to the metacarpal heads.

The cast is reapplied to the hand to test the fit, and any necessary further cuts are made. A fleece edger fabric 20 is removed from the box 24 and used to cover and protect the raw edges around the periphery of the cast. For light compression, edema control or if patient compliance is a concern, the cast is secured with a cohesive bandage from the kit 10 is used. Otherwise, the length of adhesive hook touch fastener 18 is attached to the outer surface of the cast and lengths of loop touch fastener 16 is then used to secure the cast to the arm and hand, as shown. Additional padding 22 can be added beneath the cast to protect bony prominences to reduce pressure points.

FIG. 13 illustrates a humeral cast 34 fabricated using components of the kit and the method steps according to one preferred embodiment of the invention. The terry liner 14 is removed from the box 24 and applied with the padded side next to the patient's skin. If needed, additional padding can be applied, including additional padding on the humeral head. A protective cutting strip 16 is inserted under the liner 14 extending from the humeral head to the lateral epicondyle. The cast tape 12 is removed from the box 24, removed from the moisture-proof package and activated by wetting while wearing gloves. Three layers of a reinforcing strip 18 may be cut from the cast tape 12 and applied from the humeral head to the lateral epicondyle. The cast tape 12 is then wrapped onto the arm beginning at the lower humerus and continuing proximally up the arm to the humeral head, overlapping by about 50 percent. The cast tape 12 is smoothed onto the arm, and conformed into the correct position. After the cast tape 12 has set, a marker such as a felt-tip pen is used to draw the desired cutting lines to customize the fit of the cast. The cast 34 is removed by placing cast shears between the terry liner 14 and the cutting strip 16 and cutting along the entire length of the anterior side of the upper arm. The cast can then be removed by spreading the cast along the cut line and making further comfort cuts proximal to the antecubital and distal to the epicondyles.

The cast is reapplied to the arm to test the fit, and any necessary further cuts are made. A fleece edger fabric 20 is removed from the box 24 and used to cover and protect the raw edges around the periphery of the cast. For light compression, edema control or if patient compliance is a concern, the cast is secured with a cohesive bandage from the kit 10 is used. Otherwise, the length of adhesive hook touch fastener 18 is attached to the outer surface of the cast and lengths of loop touch fastener 16 is then used to secure the cast to the arm and hand, as shown. Additional padding 22 can be added beneath the cast to protect bony prominences to reduce pressure points.

Figure 14:
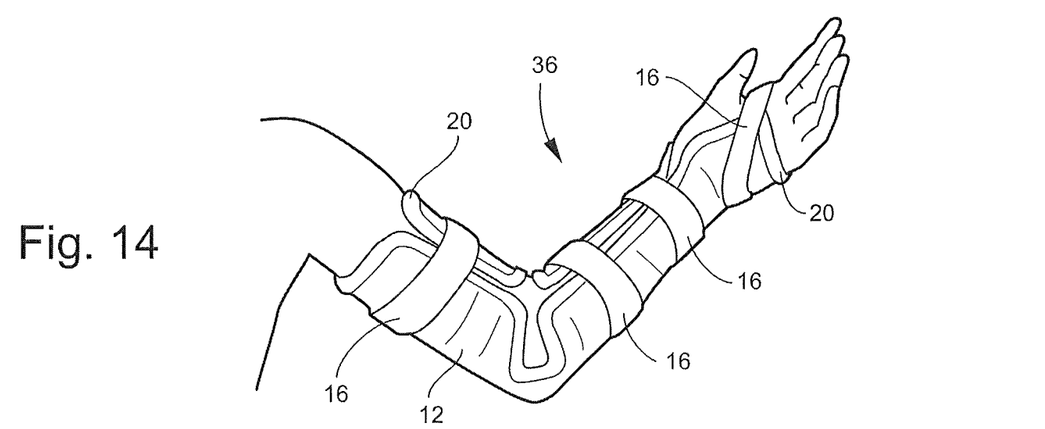
FIG. 14 is a view of a long arm cast fabricated using components of the kit and the method steps according to one preferred embodiment of the invention.

FIG. 14 illustrates a long arm cast 36 fabricated using components of the kit 10 and the method steps according to one preferred embodiment of the invention. The terry liner 14 is removed from the box 24 and applied with the padded side next to the patient's skin from the fingertips to one inch distal of the epicondyles. If needed, additional padding can be applied, including additional padding on the ulnar styloid and epicondyles. A protective cutting strip 16 is inserted under the liner 14 extending from the anterior of the hand to the lateral epicondyle. The cast tape 12 is removed from the box 24, removed from the moisture-proof package and activated by wetting while wearing gloves. A three-layer reinforcing strip 18 may be cut from the cast tape 12 and applied from anterior of the hand to approximately the lateral epicondyle. The cast tape 12 is then wrapped onto the arm beginning at the fingers and continuing proximally up the arm to about one hand width from the humeral head, overlapping by about 50 percent. The cast tape 12 is smoothed onto the arm, and conformed into the correct position. After the cast tape 12 has set, a marker such as a felt-tip pen is used to draw the desired cutting lines to customize the fit of the cast. The cast 36 is removed by placing cast shears between the terry liner 14 and the cutting strip 16 and cutting along the entire length of the anterior side of the arm. The cast can then be removed by spreading the cast along the cut line and making further comfort cuts proximal to the palmer crease and to round off any rough or sharp edges.

The cast is reapplied to the arm to test the fit, and any necessary further cuts are made. A fleece edger fabric 20 is removed from the box 24 and used to cover and protect the raw edges around the periphery of the cast. For light compression, edema control or if patient compliance is a concern, the cast is secured with a cohesive bandage from the kit 10 is used. Otherwise, the length of adhesive hook touch fastener 18 is attached to the outer surface of the cast and lengths of loop touch fastener 16 is then used to secure the cast to the arm and hand, as shown. Additional padding 22 can be added beneath the cast to protect bony prominences to reduce pressure points.

Figures 15, 16:
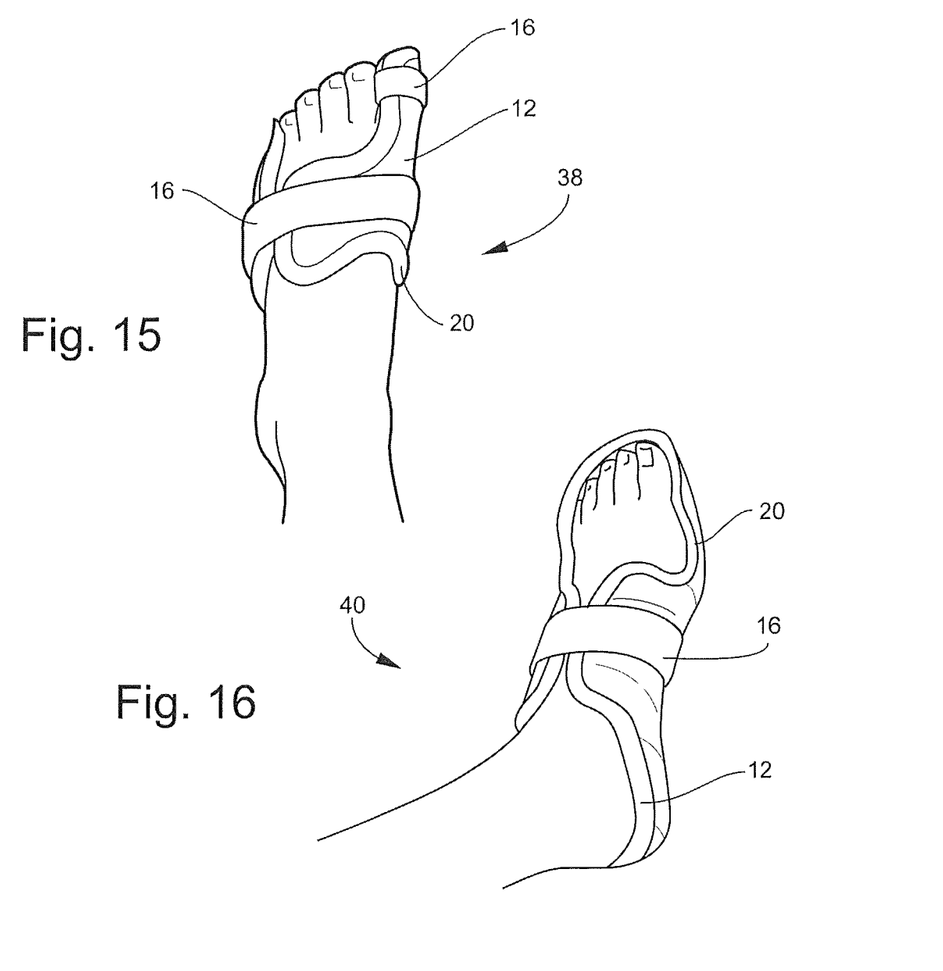
FIG. 15 is a view of a great toe cast fabricated using components of the kit and the method steps according to one preferred embodiment of the invention.
FIG. 16 is a view of a metatarsal shoe fabricated using components of the kit and the method steps according to one preferred embodiment of the invention.

FIG. 15 illustrates a great toe cast 38 fabricated using components of the kit 10 and the method steps according to one preferred embodiment of the invention. The terry liner 14 is removed from the box 24 and applied with the padded side next to the patient's skin from beyond the great toe to above the ankle. If needed, additional padding can be applied, including additional padding on bony prominences. A protective cutting strip 16 is inserted under the liner 14 on the lateral side of the foot. The cast tape 12 is removed from the box 24, removed from the moisture-proof package and activated while wearing gloves. A three-layer reinforcing strip 18 may be cut from the cast tape 12 and applied from the middle of the great toe to two finger widths proximal to the large metatarsal joint. The cast tape 12 is then wrapped onto the foot from the distal end of the metatarsals to 2 inches from the heel, overlapping by about 50 percent. The cast tape 12 is smoothed onto the foot, and conformed into the correct position. After the cast tape 12 has set, a marker such as a felt-tip pen is used to draw the desired cutting lines to customize the fit of the cast. The cast 38 is removed by placing cast shears between the terry liner 14 and the cutting strip 16 and cutting along the entire length of the lateral side of the foot. The cast can then be removed by spreading the cast along the cut line and making further comfort cuts by removing the section covering the $2^{nd}$ through $5^{th}$ metatarsals, exposing the toes except for the great toe.

The cast is reapplied to the foot to test the fit, and any necessary further cuts are made. A fleece edger fabric 20 is removed from the box 24 and used to cover and protect the raw edges around the periphery of the cast. For light compression, edema control or if patient compliance is a concern, the cast is secured with a cohesive bandage from the kit 10 is used. Otherwise, the length of adhesive hook touch fastener 18 is attached to the outer surface of the cast and a length of loop touch fastener 16 is then used to secure the cast to the arm and hand, as shown. Additional padding 22 can be added beneath the cast to protect bony prominences to reduce pressure points.

FIG. 16 illustrates a metatarsal shoe 40 fabricated using components of the kit 10 and the method steps according to one preferred embodiment of the invention. The terry liner 14 is removed from the box 24 and applied with the padded side next to the patient's skin from beyond the great toe to above the ankle. If needed, additional padding can be applied, including additional padding on the metatarsal heads on the plantar surface and sole to cover the inner and outer edges of the foot. A protective cutting strip 16 is inserted under the liner 14 along the top of the foot. The cast tape 12 is removed from the box 24, removed from the moisture-proof package and activated by wetting while wearing gloves. A three-layer reinforcing strip 18 may be cut from the cast tape 12 and applied to the sole starting at the metatarsals and extending to the heel area. The cast tape 12 is then wrapped onto the foot from the distal end of the metatarsals to 2 inches from the heel, overlapping by about 50 percent. The cast tape 12 is smoothed onto the foot, and conformed into the correct position. After the cast tape 12 has set, a marker such as a felt-tip pen is used to draw the desired cutting lines to customize the fit of the cast. The cast 40 is removed by placing cast shears between the terry liner 14 and the cutting strip 16 and cutting along the entire length of the top of the foot. The cast can then be removed by spreading the cast along the cut line and making further comfort cuts by removing the section covering the metatarsals and three finger lengths proximal to the metatarsal heads on the dorsum of the foot, exposing the toes.

The cast is reapplied to the foot to test the fit, and any necessary further cuts are made. A fleece edger fabric 20 is removed from the box 24 and used to cover and protect the raw edges around the periphery of the cast. For light compression, edema control or if patient compliance is a concern, the cast is secured with a cohesive bandage from the kit 10 is used. Otherwise, a length of adhesive hook touch fastener 18 is attached to the outer surface of the cast and a length of loop touch fastener 16 is then used to secure the cast to the arm and hand, as shown. Additional padding 22 can be added beneath the cast to protect bony prominences to reduce pressure points.

Figure 17:
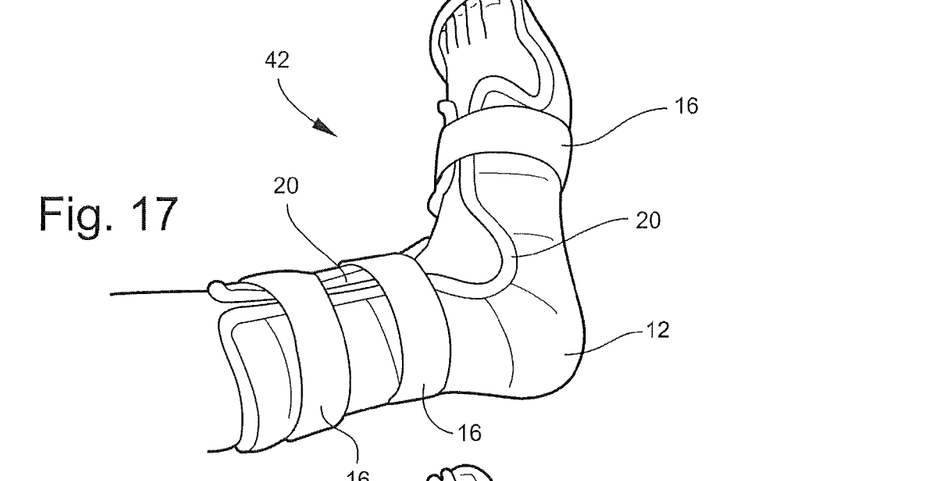
FIG. 17 is a view of a cast shoe with ankle extension fabricated using components of the kit and the method steps according to one preferred embodiment of the invention.

FIG. 17 illustrates a cast shoe with ankle extension 42 fabricated using components of the kit 10 and the method steps according to one preferred embodiment of the invention. The terry liner 14 is removed from the box 24 and applied with the padded side next to the patient's skin from the beyond the great toe to above the ankle to the calf. If needed, additional padding can be applied, including additional padding on the metatarsal heads on the plantar surface and sole to cover the inner and outer edges of the foot. A protective cutting strip 16 is inserted under the liner 14 along the top of the foot and the tibia. The cast tape 12 is removed from the box 24, removed from the moisture-proof package and activated by wetting while wearing gloves. A three-layer reinforcing strip 18 may be cut from the cast tape 12 and applied to the sole starting at the large basic toe joint along the plantar/sole surface. The cast tape 12 is then wrapped onto the foot from the distal end of the metatarsals to the center of the calf, overlapping by about 50 percent. The cast tape 12 is smoothed onto the foot, and conformed into the correct position. After the cast tape 12 has set, a marker such as a felt-tip pen is used to draw the desired cutting lines to customize the fit of the cast. The cast 42 is removed by placing cast shears between the terry liner 14 and the cutting strip 16 and cutting along the entire length of the top of the foot and the tibia. The cast can then be removed by spreading the cast along the cut line and making further comfort cuts by removing the section covering the metatarsals and three finger lengths proximal to the metatarsal heads on the dorsum of the foot, exposing the toes, and notching the cast where the foot joins the lower leg.

The cast is reapplied to the foot to test the fit, and any necessary further cuts are made. A fleece edger fabric 20 is removed from the box 24 and used to cover and protect the raw edges around the periphery of the cast. For light compression, edema control or if patient compliance is a concern, the cast is secured with a cohesive bandage from the kit 10 is used. Otherwise, a length of adhesive hook touch fastener 18 is attached to the outer surface of the cast and a length of loop touch fastener 16 is then used to secure the cast to the arm and hand, as shown. Additional padding 22 can be added beneath the cast to protect bony prominences to reduce pressure points.

Figures 18, 19:
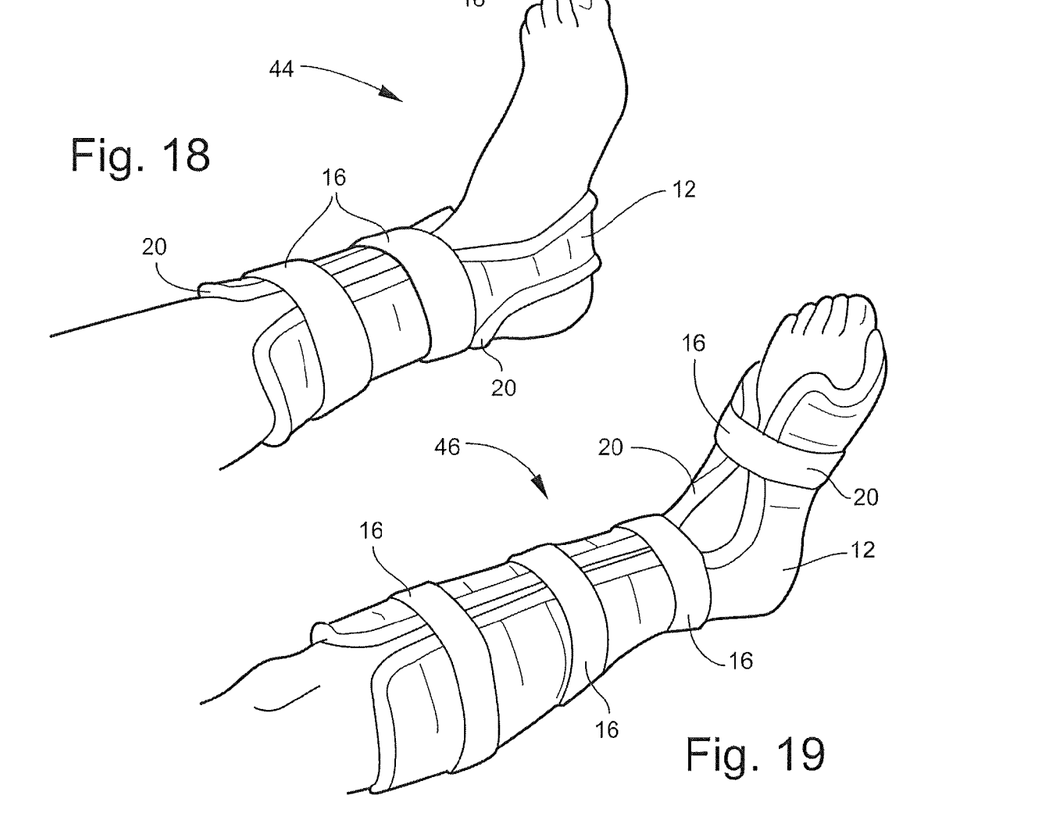
FIG. 18 is a view of an ankle stirrup fabricated using components of the kit and the method steps according to one preferred embodiment of the invention.
FIG. 19 is a view of a short leg cast fabricated using components of the kit and the method steps according to one preferred embodiment of the invention.

FIG. 18 illustrates an ankle stirrup 44 fabricated using components of the kit and the method steps according to one preferred embodiment of the invention. The terry liner 14 is removed from the box 24 and applied with the padded side next to the patient's skin from beyond the great toe to above the ankle to the calf. If needed, additional padding can be applied, including additional padding on the bony prominences on the inner and outer sides of the foot at the ankle. A protective cutting strip 16 is inserted under the liner 14 along the top of the foot and the tibia. The cast tape 12 is removed from the box 24, removed from the moisture-proof package and activated by wetting while wearing gloves. A three-layer reinforcing strip 18 may be cut from the cast tape 12 and applied across the sole and up both sides of the foot to above the ankle. The cast tape 12 is then wrapped onto the foot from the distal end of the metatarsals to the center of the calf, overlapping by about 50 percent. The cast tape 12 is smoothed onto the foot, and conformed into the correct position. After the cast tape 12 has set, a marker such as a felt-tip pen is used to draw the desired cutting lines to customize the fit of the cast. The cast 44 is removed by placing cast shears between the terry liner 14 and the cutting strip 16 and cutting along the entire length of the top of the foot and the tibia. The cast can then be removed by spreading the cast along the cut line and making further comfort cuts by removing the section covering the metatarsals and three finger lengths proximal to the metatarsal heads on the dorsum of the foot, exposing the toes, and notching the cast where the foot joins the lower leg.

The cast is reapplied to the foot to test the fit, and any necessary further cuts are made. A fleece edger fabric 20 is removed from the box 24 and used to cover and protect the raw edges around the periphery of the cast. For light compression, edema control or if patient compliance is a concern, the cast is secured with a cohesive bandage from the kit 10 is used. Otherwise, a length of adhesive hook touch fastener 18 is attached to the outer surface of the cast and a length of loop touch fastener 16 is then used to secure the cast to the arm and hand, as shown. Additional padding 22 can be added beneath the cast to protect bony prominences to reduce pressure points.

FIG. 19 illustrates a short leg cast 46 fabricated using components of the kit 10 and the method steps according to one preferred embodiment of the invention. The terry liner 14 is removed from the box 24 and applied with the padded side next to the patient's skin from beyond the great toe to above the ankle to the knee. If needed, additional padding can be applied, including additional padding on the bony prominences on the inner and outer sides of the foot at the ankle. A protective cutting strip 16 is inserted under the liner 14 along the top of the foot and the tibia. The cast tape 12 is removed from the box 24, removed from the moisture-proof package and activated by wetting while wearing gloves. A three-layer reinforcing strip 18 may be cut from the cast tape 12 and applied beginning at the basic toe joints along the plantar surface extending along the posterior of the leg ending one hand width below the knee throat. The cast tape 12 is then wrapped onto the foot and up the lower leg to three finger widths from the tibia head, overlapping by about 50 percent. The cast tape 12 is smoothed onto the foot, and conformed into the correct position. After the cast tape 12 has set, a marker such as a felt-tip pen is used to draw the desired cutting lines to customize the fit of the cast. The cast 46 is removed by placing cast shears between the terry liner 14 and the cutting strip 16 and cutting along the entire length of the top of the foot and the tibia. The cast can then be removed by spreading the cast along the cut line and making further comfort cuts by removing the section covering the metatarsals and three finger lengths proximal to the metatarsal heads on the dorsum of the foot, exposing the toes, and notching the cast where the foot joins the lower leg.

The cast is reapplied to the foot to test the fit, and any necessary further cuts are made. A fleece edger fabric 20 is removed from the box 24 and used to cover and protect the raw edges around the periphery of the cast. For light compression, edema control or if patient compliance is a concern, the cast is secured with a cohesive bandage from the kit 10 is used. Otherwise, a length of adhesive hook touch fastener 18 is attached to the outer surface of the cast and a length of loop touch fastener 16 is then used to secure the cast to the arm and hand, as shown. Additional padding 22 can be added beneath the cast to protect bony prominences to reduce pressure points.

Figure 20:
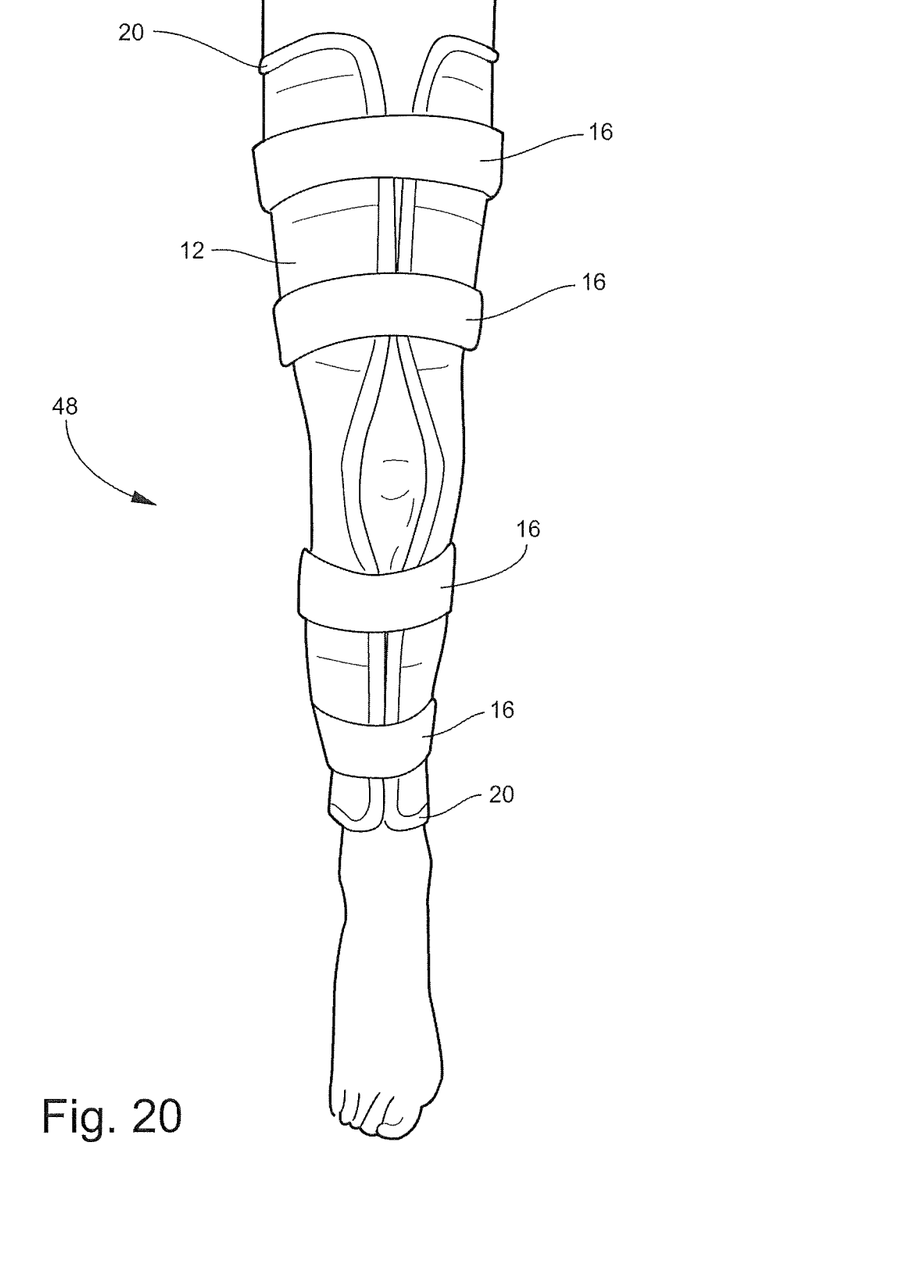
FIG. 20 is a view of a short version knee immobilizer/Tutor fabricated using components of the kit and the method steps according to one preferred embodiment of the invention.

FIG. 20 is a view of a short version knee immobilizer/Tutor 48 fabricated using components of the kit 10 and the method steps according to one preferred embodiment of the invention. The terry liner 14 is removed from the box 24 and applied with the padded side next to the patient's skin from above the ankle to below the knee. If needed, additional padding can be applied, including additional padding on the medial and lateral condyles. A protective cutting strip 16 is inserted under the liner 14 along the tibia and over the patella. The cast tape 12 is removed from the box 24, removed from the moisture-proof package and activated by wetting while wearing gloves. A three-layer reinforcing strip 18 may be cut from the cast tape 12 and centered around the knee throat extending longitudinally along the posterior of the leg. The cast tape 12 is then wrapped onto the leg from the center of the calf to the center of the thigh, overlapping by about 50 percent. The cast tape 12 is smoothed onto the foot, and conformed into the correct position. After the cast tape 12 has set, a marker such as a felt-tip pen is used to draw the desired cutting lines to customize the fit of the cast. The cast 48 is removed by placing cast shears between the terry liner 14 and the cutting strip 16 and cutting along the entire length of the top of the tibia. The cast can then be removed by spreading the cast along the cut line and making further comfort cuts by trimming material to expose the patella and rounding any rough edges.

The cast is reapplied to the foot to test the fit, and any necessary further cuts are made. A fleece edger fabric 20 is removed from the box 24 and used to cover and protect the raw edges around the periphery of the cast. For light compression, edema control or if patient compliance is a concern, the cast is secured with a cohesive bandage from the kit 10 is used. Otherwise, a length of adhesive hook touch fastener 18 is attached to the outer surface of the cast and a length of loop touch fastener 16 is then used to secure the cast to the arm and hand, as shown. Additional padding 22 can be added beneath the cast to protect bony prominences to reduce pressure points.

The above examples are not exhaustive, and many other cast types can be created using a kit as described and the method steps described.

Lengths and quantities of the kit components may vary depending on the type of cast to be fabricated. Most casts can be fabricated using 36 in. (90 cm.) of terry liner or cast padding, 30-36 in. (76-90 cm.), 12 in. (30 cm.) of adhesive hook material and 24 in. (60 cm.) of stretch loop material, all 1 in. (2.5 cm) wide. Several 2 in. by 2 in. (5 cm. by 5 cm.) foam pads provide additional padding on bony prominences.

A functional cast therapy product, and a method of using the product to create a therapeutic cast on a patient according to several embodiments of the invention have been described with reference to specific examples, which are not intended to be exclusive, and are not exclusive. Various details of the invention may be changed without departing from the scope of the invention. Furthermore, the foregoing description of the preferred embodiments of the invention and best mode for practicing the invention are provided for the purpose of illustration only and not for the purpose of limitation, the invention being defined by the claims.

I claim:

1. A kit containing components for fabricating functional casts, comprising:
   (a) a length of liner for being placed next to the skin of the body part to be immobilized;
   (b) a moisture-proof package containing a length of cast tape of the type impregnated with a moisture-curable resin that remains in a flexible, comfomable state until activated and hardened into a rigid state by exposure to moisture;
   (c) at least one strap for securing the cast onto the body part being immobilized; and
   (d) a length of adhesive edger material that is a separate component from the liner and cast tape and is adapted to adhere to, surround, and enclose raw edges of the hardened cast tape to protect skin of the cast wearer from exposure to the cast tape.

2. A kit according to claim 1, and including at least one pad for being placed between the cast tape and the body part to provide additional protection to bony prominences.

3. A kit according to claim 1, wherein the at least one strap comprises a length of loop touch fastener material and a length of complementary touch fastener hook material and the at least one strap is not integrally formed with the east tape.

4. A kit according to claim 3, wherein the length of loop touch fastener is stretchable, and the length of hook material has an adhesive on one side for being attached to the cast tape.

5. A kit according to claim 1, wherein the liner is a material selected from the group consisting of a terry cloth stockinette and a water resistant cast padding.

6. A kit according to claim 1, wherein the edger material comprises a moisture resistant fleece material with an adhesive on one side for being adhered to the cast tape.

7. A kit according to claim 1, and including a length of protective cutting strip for being applied to the body part under the liner.

8. A kit containing components for fabricating functional casts, comprising:
   (a) a length of liner selected from the group consisting of a terry cloth stockinette and a water resistant cast padding for being placed next to the skin of the body part to be immobilized;
   (b) a moisture-proof package containing a length of cast tape of the type impregnated with a moisture-curable resin that remains in a flexible, comformable state until activated and hardened into a rigid state by exposure to moisture;

(c) a length of stretchable loop touch fastener material and a length of complementary touch fastener adhesive hook material;

(d) at least one pad for being placed between the cast tape and the body part to provide additional protection to bony prominences;

(e) a length of adhesive fleece edger material that is a separate component from the liner and cast tape and is adapted to adhere to, surround, and enclose for enclosing raw edges of the hardened cast tape for protecting the skin of the cast wearer from exposure to the cast tape; and (f) a suitably-sized package for containing (a)-(e) in kit form until use.

9. A kit according to claim 8, wherein the package comprises a box.

10. A method of fabricating a functional cast, comprising the steps of:

(a) providing a kit containing components for fabricating functional casts, comprising a length of liner for being placed next to the skin of the body part to be immobilized, a length of cutting strip, a moisture-proof package containing a length of cast tape of the type impregnated with a moisture-curable resin that remains in a flexible, comformable state until activated and hardened into a rigid state by exposure to moisture, at least one strap for securing the cast onto the body part being immobilized, and a length of adhesive edger material for enclosing raw edges of the hardened cast tape for protecting the skin of the cast wearer from exposure to the cast tape;

(b) removing the liner from the kit and applying the liner to a body part to be immobilized;

(c) inserting the length of cutting strip between the liner and the body part;

(d) removing the moisture-curable cast tape from the package, activating the moisture-curable resin with water and applying the cast tape to the body part to form a cast when hardened;

(e) when hardened, cutting along a line defined by the length of the cutting strip;

(f) spreading the cast and removing it from the body part;

(g) cutting the cast as needed to customize the fit to the body part; (h) applying edger material to raw edges of the cast tape;

(i) re-applying the cast to the body part; and (j) securing the cast to the body part.

11. A method according to claim 10, wherein the step of securing the cast to the body part includes the steps of providing in the kit a length of stretchable loop touch fastener material and a length of complementary touch fastener adhesive hook material, adhering the hook touch fastener to the cast, wrapping the loop touch fastener around the cast and adhering the loops to the hooks.

12. A method according to claim 10, and including the steps of providing padding material in the kit, removing the padding from the kit and inserting the padding under the cast tape in an area defined by a bony prominence.

13. A method according to claim 10, wherein the fabricated cast is selected from the group consisting of a forearm functional cast, short thumb spica cast, teardrop hand splint, boxer hand splint, humeral cast, long arm cast, great toe cast, metatarsal shoe, cast shoe with ankle extension, ankle stirrup, short leg, and short version knee immobilizer/Tutor cast.

* * * * *

UNITED STATES PATENT AND TRADEMARK OFFICE
CERTIFICATE OF CORRECTION

PATENT NO. : 9,504,597 B2
APPLICATION NO. : 14/196226
DATED : November 29, 2016
INVENTOR(S) : Thomas D. Darcey It is certified that error appears in the above-identified patent and that said Letters Patent is hereby corrected as shown below:

In the Claims

Column 13, Line 12, after "and enclosed" delete "for enclosing".

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*